(12) United States Patent
Tobias et al.

(10) Patent No.: US 6,411,103 B1
(45) Date of Patent: Jun. 25, 2002

(54) STRAY-FIELD SENSOR

(75) Inventors: Jörg Tobias, Drage; Reinhard Knöchel, Elmshorn; Matthias Busse, Kiel, all of (DE)

(73) Assignee: Hauni Maschinenbau AG, Hamburg (DE)

( * ) Notice: Subject to any disclaimer, the term of this patent is extended or adjusted under 35 U.S.C. 154(b) by 96 days.

(21) Appl. No.: 09/587,516

(22) Filed: Jun. 5, 2000

(30) Foreign Application Priority Data

Jun. 3, 1999 (DE) .......................... 199 25 468

(51) Int. Cl.[7] ............................... G01R 27/04
(52) U.S. Cl. ...................................... 324/632
(58) Field of Search .................. 324/632, 633, 324/634, 636, 637, 640, 643, 658, 663, 664, 687; 340/870.37; 73/862.626; 250/332; 343/841; 361/816, 818

(56) References Cited

U.S. PATENT DOCUMENTS 5,334,941 A * 8/1994 King ........................... 324/637
5,397,993 A    3/1995 Tews et al.
6,249,130 B1 * 6/2001 Greer ........................... 324/687

FOREIGN PATENT DOCUMENTS

| DE | 197 05 260 | 8/1997 |
| DE | 197 34 978 | 2/1999 |
| DE | 198 54 550 | 5/2000 |
| EP | 0 558 759 | 9/1993 |
| WO | 99/02979 | 1/1999 |

OTHER PUBLICATIONS

U.S. application No. 09/447,794, Schröder et al., filed Nov. 23, 1999.

* cited by examiner

*Primary Examiner*—Safet Metjahic
*Assistant Examiner*—Etienne LeRoux
(74) *Attorney, Agent, or Firm*—Venable; Robert Kinberg

(57) ABSTRACT

A stray-field sensor for measuring dielectric properties of substances includes generating elements for generating an electrical field and shielding elements for shielding the generated electrical field. The shielding elements have at least two openings for coupling the electrical field out into the outside space so that the electrical field is at least partially located outside of the shielding elements.

27 Claims, 6 Drawing Sheets

STRAY-FIELD SENSOR

Priority is claimed with respect to Application No. 199 25 468.0 filed in Germany on Jun. 3, 1999, the disclosure of which is incorporated herein by reference.

BACKGROUND OF THE INVENTION

The invention relates to a stray-field sensor for measuring dielectric properties of substances, having generating elements for generating an electrical field, and shielding elements for shielding the generated electrical field, the shielding elements being configured such that the electrical field is located at least partially outside of the shielding elements.

Stray-field sensors of this type are known. The known stray-field sensors employ an electromagnetic stray field to measure dielectric properties of substances located in the electromagnetic stray field. For example, these stray-field sensors can be used to measure the effective dielectric constant of a substance for indirectly drawing conclusions about the type of substance, its moisture content, density, etc. To promote a better understanding of these stray-field sensors, and particularly of the present invention, the general technical background of the sensors is discussed below.

The aforementioned stray-field sensors are more commonly referred to as dielectrometer sensors. Dielectrometer sensors of this type preferably generate an electrical, high-frequency AC field. The substance to be examined is then brought into the high-frequency AC field, which increases the displacement current. A capacitor made in this manner is preferably a component of a resonant circuit. This resonant rise of the field intensity increases the sensitivity of the dielectrometer sensor with respect to ascertaining changes in the dielectric constant. A dielectric constant that increases when the substance to be examined is brought in lowers the resonant frequency, while losses in the substance to be examined damp the resonance.

There are two possible ways to examine the substance. First, the substance to be examined can be brought into the resonator. This method is known from, for example, from German application DE 197 05 260 A1 and the associated supplemental application DE 197 34 978 A1, both owned by the assignee of the present application. In the apparatuses described therein, the resonator of the dielectrometer sensor is disposed in a housing having an entrance opening and an exit opening. A rope of tobacco, particularly a cigarette rope, can be guided through the entrance or exit opening of the apparatus described here. Thus, in this apparatus, when the cigarette rope is guided through the resonator, this influences the resonant frequency of the resonant circuit, and permits a measurement of the properties of the cigarette rope, such as its moisture content or density. The cited documents also describe a method (not reiterated here) for precisely measuring these resonance shifts.

The cited arrangements and methods for measuring the density of a substance, particularly for measuring the density of a tobacco rope, have been proven effective because the cited methods and arrangements can be used to measure density in a control circuit, which simultaneously influences the density. Hence, these apparatuses can be used in the precise determination of the density of a substance to be examined, for example, the aforementioned tobacco rope.

The method described in the cited documents measures the resonance value at at least two points on the resonance curve of the resonator through which the substance is guided. In addition to the average value of the measured values and the difference, the dielectric properties, such as the moisture content of the substance and, consequently, the density of the substance, can be calculated.

In the tobacco-processing industry, it is particularly desirable to measure the moisture content of the substance to be examined as early as possible. Thus, in the tobacco-processing industry, it is desirable to examine the tobacco while it is still in bulk form, or before it has been rolled. This is because it is only at this point that the moisture content of the tobacco can still be influenced satisfactorily. If the tobacco has already been processed into a rope, the moisture content of the processed tobacco can no longer be influenced satisfactorily. It is therefore necessary to guide the substance to be examined past the resonator, which emits a stray field, rather than insert the substance as a sample into the resonator itself. The present invention, notably the stray-field sensor of the present invention, relates to this type of embodiment of a resonator.

In stray-field sensors of this type, the substance to be examined is guided through a stray field present outside of the actual resonator. For this purpose, the resonator is preferably embodied such that its electrical field is at least partially located outside of a shielding element, while the remainder of the electrical field, and the magnetic field, are located within the shielding element, so they do not interact with the substance to be examined, for example, the bulk tobacco to be examined. Thus, in the stray-field sensors of the type mentioned at the outset, only a portion of the electrical field, which is located inside the shielding element, is coupled into the outside space. Measuring in the microwave range has proven especially advantageous in measuring the moisture content of substances to be examined, for example the moisture content of tobacco.

For utilizing such stray-field sensors in precisely ascertaining the aforementioned losses in the substance to be examined, it is necessary to avoid emission losses of the stray-field sensor. This is imperative because, in non-magnetic materials, besides the losses in the substance to be examined, only dielectric losses occur in addition to known ohmic losses in the conductors. Dielectric losses are the objective of the measurement. It is therefore advisable to suppress the emission losses to the greatest possible extent. A suppression of the emission losses means that the far field of the electrical field is suppressed, so only a near field is still present in the vicinity of the stray-field sensor. The aforementioned emission losses are notably avoided if the emission components of the far field are canceled out for as many angular positions as possible due to their phase opposition. This mutual cancellation of the emission components in the far field is only possible, however, if the diameter of the opening through which the stray field exits the shielding elements of the stray-field sensor is significantly smaller than the used wavelength. A drawback of this is that, because of the small diameter of the stray-field openings in the stray-field sensor, measurements of the moisture content of the substance to be examined, for example, can only be taken in this region. Therefore, stray-field sensors of this design, that is, stray-field sensors having small openings, produce only point-wise measurements of the dielectric constants of the substance to be examined. This is also disadvantageous if the substance to be examined is non-homogeneous. This lack of homogeneity is characteristic of bulk goods, for example. In loose tobacco, for example, as is used by the tobacco-processing industry, the arbitrary arrangement of the individual tobacco fibers in the loose tobacco presents a severe non-homogeneity. Stray-field sensors that measure point-wise can only provide imprecise measurements of the moisture content of such non-homogeneous tobacco.

To overcome the above-described disadvantage, it has been proposed to use a plurality of such stray-field sensors. The use of a plurality of stray-field sensors or resonators permits the approximate determination of the moisture content of leaf tobacco, for example, which is often partly not in climatic equilibrium, even with a non-uniform moisture distribution in the individual tobacco leaf; specifically, the plurality of stray-field sensors determines the moisture content. An arrangement of numerous sensors is known from, for example, EP-A-0 558 759 A1.

A drawback of the described arrangement of a plurality of resonators or stray-field sensors is that, if measurements are taken in the microwave range, for example, the microwaves must be divided via a power divider and re-mixed behind the resonators or sensors. This requires a high outlay for components. Furthermore, this type of measuring arrangement requires the use of high-quality resonators to ensure that all resonators operate at the same frequency. All in all, overcoming the problems of emissions in this arrangement is associated with a high technical outlay.

SUMMARY OF THE INVENTION

It is therefore an object of the invention to improve a stray-field sensor of the type mentioned at the outset to avoid the above-described disadvantages and make available a stray-field sensor that can reliably examine the dielectric properties of even non-homogeneous substances or bulk items, particularly their moisture content, and has a simple design.

In a stray-field sensor of the type mentioned at the outset, this object is accomplished in that the shielding elements have at least two openings for coupling out the electrical field.

The coupling out of the stray field at two locations of the shielding elements advantageously permits the examination of the dielectric properties of non-homogeneous substances, even with small openings/locations through which the stray field exits to the outside, namely comes into contact with the substance to be examined. These dielectric properties then reveal the moisture content of the substance to be examined. Thus, with the invention, it is possible to use a sufficient number of locations for coupling out the electrical field or coupling the electrical field with the substance to be examined in order to take the mean of the individual measured values, and thereby obtain a more precise measured value than was possible in the aforementioned known stray field sensors. This is even the case with non-homogeneous substances, such as leaf tobacco, which has a non-homogeneous moisture and density distribution. In particular, the invention also avoids the disadvantages ensuing from the arrangement of a plurality of independent stray-field sensors according to EP-A-0 558 759 A1, because the invention eliminates the necessity of an identical design of the individual sensors and the division and re-mixing of the electromagnetic waves in front of and behind the sensor, respectively.

The invention employs a single stray-field sensor, or a single stray-field resonator, and simultaneously couples the stray field out into the outside space at a number of locations. Thus, it is possible to cover a large surface area with a resonator of the invention without the drawbacks of large openings, i.e., emissions. The invention is therefore well-suited for use in the tobacco-processing industry, in which, as mentioned several times already, it is critical to analyze the loose tobacco or leaf tobacco, which is non-homogeneous with respect to density and moisture content.

With the invention, an analysis of this type is possible in a simple manner, and with high precision.

The electromagnetic field generated by the generating elements is preferably a high-frequency AC field. The generating elements are preferably embodied such that the stray-field sensor constitutes a resonator, that is, the high-frequency AC field is in resonance. The measuring method used in this connection, and the precise taking of measurements, are known from the cited German patent applications DE 197 05 260 A1 and DE 197 34 978 A1. They are not described again here, because a person of skill in the field of microwave measuring technology can easily apply the method described therein to the present invention.

In a preferred embodiment of the invention, the shielding elements are embodied as a housing for the generating elements. The openings are configured as holes in the housing. The housing preferably comprises metal.

In an especially preferred embodiment, the electrical field is coupled out at points of identical amplitude of the electrical field due to the arrangement of the openings in the shielding elements or the housing at the points of identical amplitude. It is especially preferable for the locations of identical amplitude to be identical-polarity maxima of the electrical field. Due to the interruption of the shielding of the resonant electrical field at locations of the half-wave electrical-field maxima of the same polarity, a portion of the electrical field is coupled as a stray field outside of the shielding elements such that each coupling out, in and of itself, does not radiate, that is, no far field is present. In this way, the present embodiment of the invention advantageously limits the stray field to the immediate vicinity of the stray-field sensor with this embodiment. The identical poling of the electrical stray-field components exiting the stray-field sensor prevents a long connecting field line between the stray-field components exiting the different openings in the shielding elements because there is no difference in potential between stray-field components exiting the individual openings in the shielding elements; such a field line would otherwise result in an emission.

A particular advantage of this embodiment is that there is no need for rows of numerous stray-field sensors or stray-field resonators. Instead, with the invention, a single stray-field resonator is sufficient in this embodiment to make available a plurality of measuring points by way of the numerous openings, so non-homogeneous objects can also be measured. Thus, this embodiment also permits the measurement of, for example, leaf tobacco or loose tobacco having a non-homogeneous density and moisture distribution.

In a further embodiment of the invention, the generating elements for generating the resonant electrical field are embodied as a waveguide. The waveguide is preferably embodied as a line resonator through a short-circuit at its two ends. The length of the waveguide is preferably selected to be a whole-number multiple of one-half of the wavelength. The waveguide length is especially preferably three times one-half of the wavelength, or, even more preferably, at least ten times one-half of the wavelength at resonance. In these embodiments, simple means can assure an arbitrary number of measurement points. To provide an entire surface with measurement points, for example, the line resonator can have a meandering design. This permits a maximum number of measurement points to be provided per surface. The surface is preferably the surface of a wall past which the bulk item, for example, the loose tobacco to be measured, is guided.

A different preferred embodiment includes a cross-shaped waveguide. Here, it is especially preferred for the whole-number multiple of one-half of the wavelength, which constitutes the total length of the cross-shaped waveguide, to be an uneven whole-number multiple of one-half of the wavelength. This is because, in this type of embodiment, the electrical field, for example a microwave field, can be coupled into the center of the line. This type of arrangement, which can also be selected in a meandering arrangement of the waveguide, prevents additional resonances at different frequencies from the desired resonant frequency if the waveguide is fairly long. Such resonances can cause mutually-interfering resonances if the waveguide is fairly long, or if there are many openings in the shielding elements, for example, in the housing of the resonator acting as a generating element. In this regard, selecting the waveguide length to be an uneven multiple of one-half of the wavelength is an advantageous countermeasure. A commensurate field maximum exists in the center of the line resonator. If the field is coupled into the line resonator at this point, all resonances for which n is even are suppressed, because they have a zero field value. The suppression of undesired resonances is also assured in other embodiments that provide an arbitrary coupling of the electrical field, which is symmetrical to the center of the waveguide, into the line resonator.

In the aforementioned cross-shaped arrangement of the line resonator, it is especially preferable for the length of each leg of the cross to correspond to five times one-half of the wavelength of the resonance. This enables the provision of five measurement points, or openings, in the housing for the line resonator, including a measurement point in the center. This embodiment of the invention is particularly simple and compact, and simultaneously provides a sufficient number of measurement points.

In the aforementioned cross-shaped embodiment of the waveguide, the spacing between the actual line resonator and the housing surrounding the line resonator is preferably established by pins that are connected to the line resonator and extend perpendicular thereto, the pins being respectively disposed at the points where the electrical field is coupled out into the outside space. This allows the stray field to be coupled out especially simply into the outside space in order to interact with the substance to be measured. It must be considered that the line length of the pins leading from the line resonator to the respective measuring window, or opening, contributes to the length of the waveguide or line resonator.

It is particularly preferable for the waveguide to be highly resistive. This attains an especially high quality of the line resonator formed by the waveguide, so the measurement results are likewise of high quality.

In a further embodiment of the invention, the electrical field is coupled into the housing through openings in the housing surrounding the line resonator. Corresponding antennas serve in the coupling-in and coupling-out processes. As mentioned above, the electrical field is preferably coupled into the center of the resonator. The coupling out can take place in the vicinity of the line ends of the line resonator, although this is not absolutely necessary, because the conversion into the suppressed interference modes is low there. On a related note, a symmetrical arrangement of the coupling-out antennas, i.e. a symmetrical coupling out, avoids such a conversion.

In a preferred embodiment, a cavity resonator constitutes the generating element for generating the electrical resonant field. In this case as well, the electrical field is preferably coupled into the center of the cavity resonator. In the cavity resonator, the generated electrical resonant field is coupled into the outside space, or the object to be measured, via antennas. These antennas are preferably embodied as cylinders comprising a dielectric material, but more preferably as Plexiglas cylinders.

DETAILED DESCRIPTION OF THE INVENTION

Figure 1:
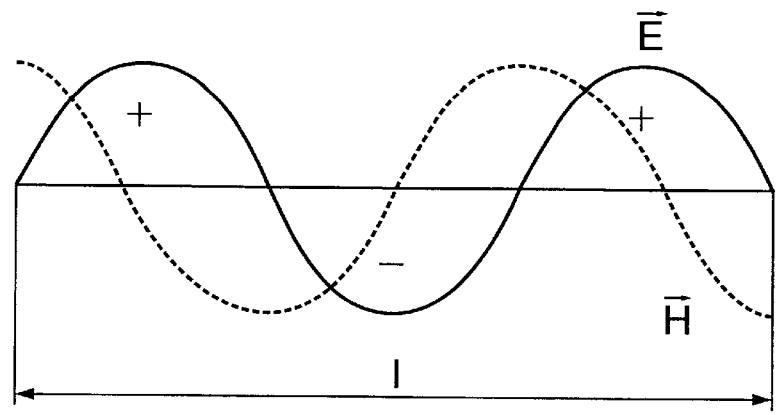
FIG. 1 is a signal diagram illustrating a principle underlying the invention.

FIG. 1 is a signal diagram illustrating a principle of the present invention. The letter E symbolizes the electrical field. The letter H represents the corresponding magnetic field. The letter I symbolizes the length of the waveguide used in this embodiment. The operational signs "+" and "−" represent half-waves of the electrical field E, which are of identical polarity, respectively. According to the invention, the openings in the shielding element of the invention are disposed at the locations of the shielding element that are adjacent to the amplitude maxima of the electrical field E represented by +.

Figure 2:
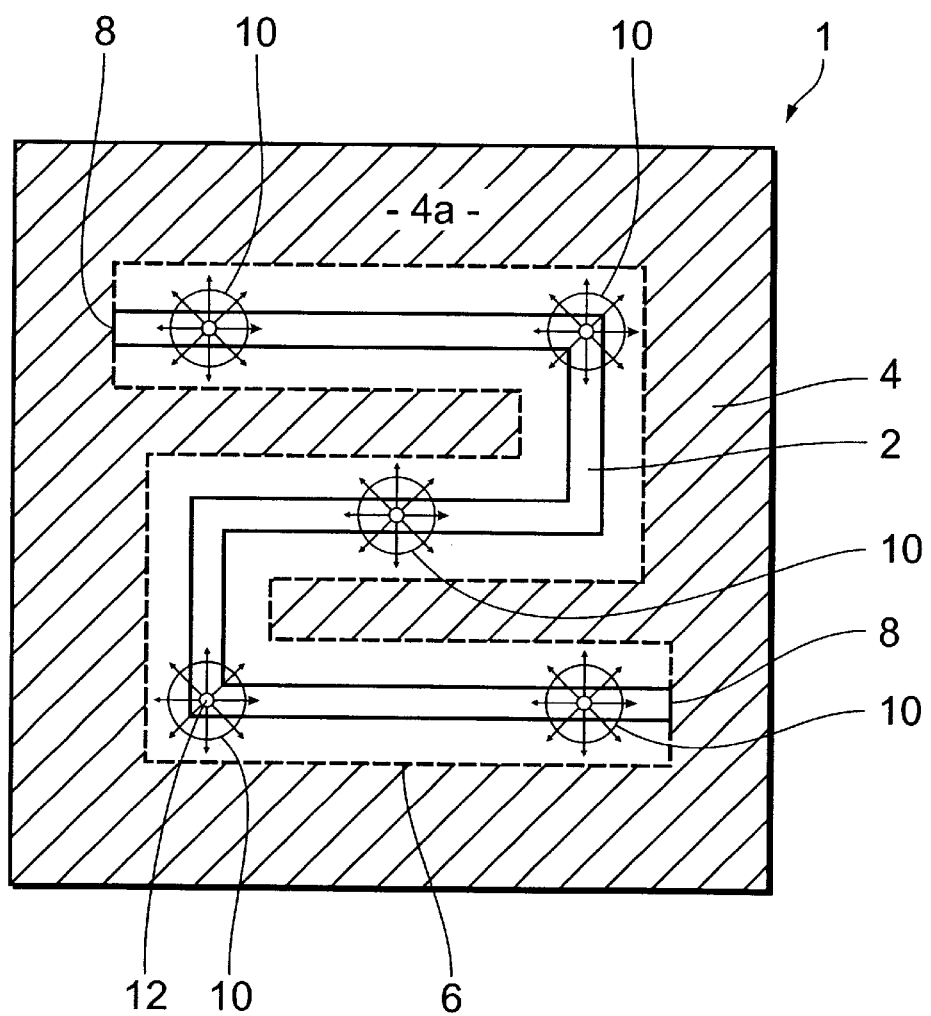
FIG. 2 is a schematic showing a top, cut away view of an embodiment of the invention with a meandering waveguide.

FIG. 2 is a schematic plan view of an embodiment of the invention with a meandering line resonator 2. The schematically-illustrated line resonator 2 is disposed in a plane that extends parallel to the paper plane of FIG. 2. The line resonator 2 is located inside a housing 4. The housing 4 has a wall 4a, which faces the view in FIG. 2. The wall 4a is broken open inside the dashed line 6 to provide a clear view of the meandering line resonator 2.

The line resonator 2 is a dielectric waveguide that is short-circuited at its ends 8 to form the line resonator 2.

The housing 4 additionally has openings 10. The openings 10 are circular. The diameter of the openings 10 is small relative to the resonance wavelength generated by the line resonator 2. In the region of the openings 10, the small arrows extending radially from the center point of the openings 10 represents the electrical stray field being coupled out of the line resonator 2 at these locations, through the housing wall 4a in the direction of the viewer and into the outside space. This electrical stray field is radiated by pins 12 disposed on the line resonator 2, perpendicular to the drawing plane and at the height of the center points of the openings 10. The pins 12 accordingly serve as coupling-out antennas for coupling the electrical stray field from the line resonator 2 out of the housing 4.

The arrangement of the openings 10, or the pins 12, is selected such that the openings 10 or pins 12 are located at the points of identical-polarity amplitude maxima of the electrical field generated by the line resonator 2. In terms of FIG. 1, the pins 12 are located at the amplitude maxima of the electrical field E that are represented by the operational sign "+."

Figure 3:
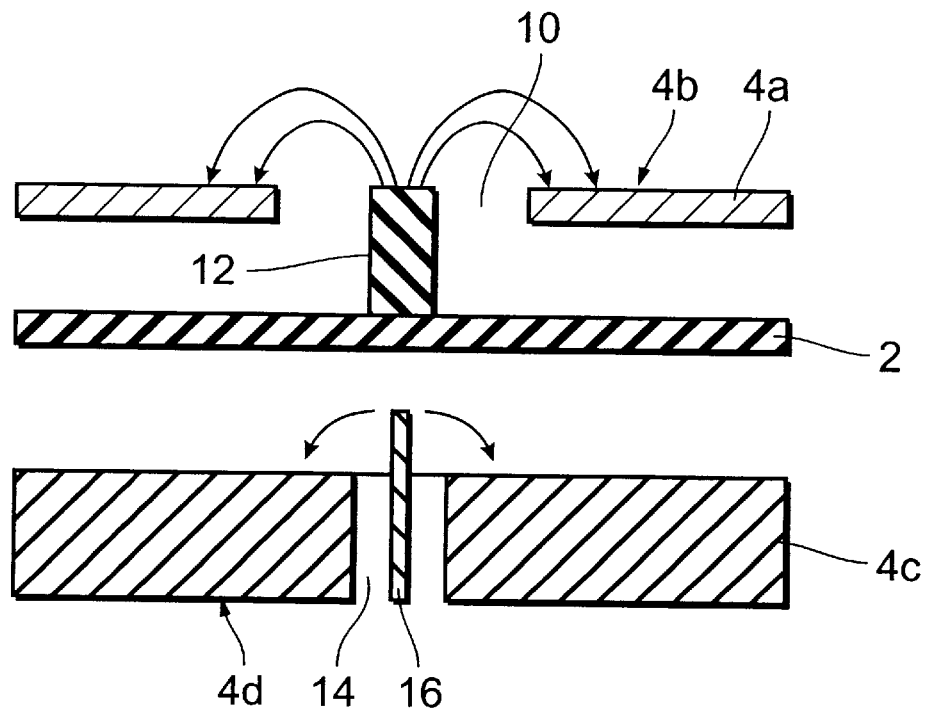
FIG. 3 is a side view of the embodiment according to FIG. 2.

FIG. 3 is a side view of the embodiment according to FIG. 2. Identical parts are provided with the same reference characters. Again, the arrows arching from the pins 12 on the line resonator 2, into the openings 10 in the housing wall 4a, to the outside, and impacting the outside 4b of the housing wall 4a represent the stray field coupled out of the line resonator 2 by means of the pins 12.

FIG. 3 also illustrates the lower wall 4c of the housing 4 serving as a shielding element. The lower wall 4c extends parallel to the upper wall 4a of the housing 4. The lower wall 4c has a central opening 14. Disposed in the opening 14 is a coupling-in antenna 16. From the coupling-in antenna 16, the field is coupled into the housing 4 and into the line resonator 2.

If a substance is to be examined for its dielectric properties, the substance is guided directly past the stray-field sensor 1 at the outside 4b of the wall 4a of the housing 4, the sensor being supplied with the electrical field via the coupling-in antenna 16. If, for example, loose tobacco is to be examined for its dielectric properties, such as moisture content, the tobacco is guided through the stray field of the line resonator 2 on the first side 4b of the wall 4a, as represented in FIG. 3 by the arrow above the wall 4a. For example, the stray-field resonator 1 can be a part of a wall that is nearly vertical, but slightly inclined with respect to the vertical wall along which the loose tobacco passes. This passage of the loose tobacco through the stray field radiated by the pins 12 changes the resonant frequency curve of the line resonator 2. This change in the resonant frequency and the damping of the resonant frequency can be ascertained with the aid of the methods and measuring structures described in the German patent applications DE 197 05 260 A1 and DE 197 34 978 A1. The average moisture content of the loose tobacco guided past the outside 4b of the wall 4a can subsequently be determined.

The housing 4 of the stray-field sensor preferably comprises a material having a low temperature-expansion coefficient. This material preferably contains an alloy composed of up to 64% iron and up to 36% nickel. The housing 4 can have a temperature-control arrangement, not shown, which keeps the operating temperature of the housing 4 at least approximately constant. This temperature-control arrangement of the housing 4 can have a sensor, not shown, for the temperature of the housing 4, the sensor controlling a transistor, also not shown, such that the thermal loss of the transistor keeps the temperature of the housing 4 at least approximately constant, preferably above ambient temperature. It is also preferable for the insides of the walls 4a, 4c and the side walls of the housing 4 to be at least partially coated with a corrosion-resistant metal, or at least partially comprise such a metal. This coating preferably consists of an electrically-conductive metal. The outside surfaces 4b, 4d and the lateral outside surfaces of the housing 4 can also be coated with a corrosion-resistant metal. This coating metal preferably contains gold. Moreover, the inside surface of outside wall 4a of the housing 4 is preferably additionally coated, at least partially, with a plastic of the polyaryl ether ketone (PEAK) group, particularly with a polyether ketone (PEEK) plastic. A further layer, not shown, comprising such a plastic can also be applied to the outside 4b of the outside wall 4a, parallel to the inside surface of outside wall 4a.

Figure 4:
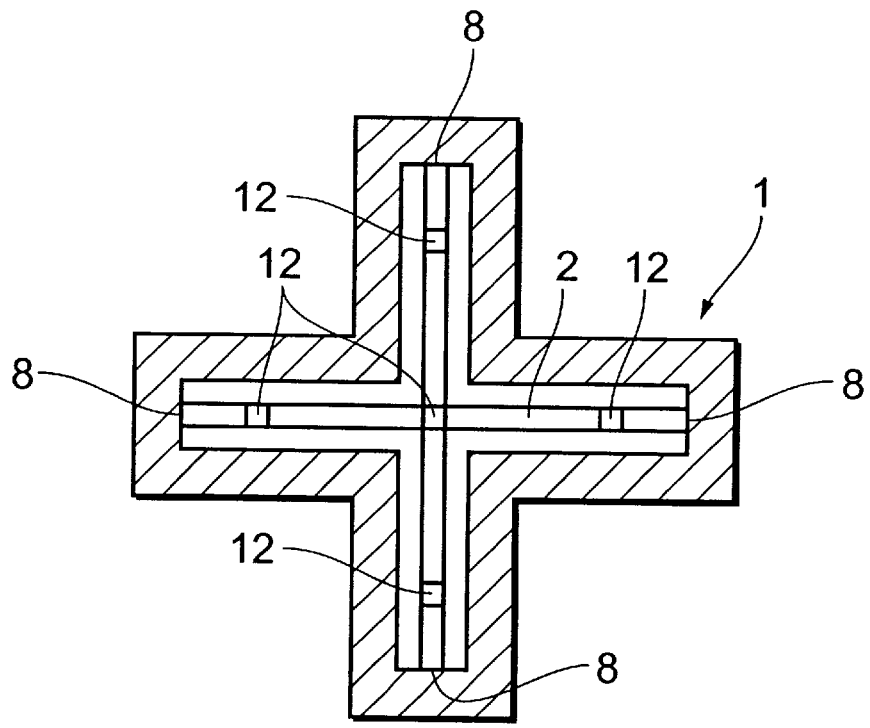
FIG. 4 is a top, cutaway view of another embodiment of the invention with a cross-shaped waveguide.

FIG. 4 shows a further embodiment of a stray-field sensor 1. Also in this case, identical parts are provided with the same reference characters. In the stray-field sensor 1 illustrated in FIG. 4, the line resonator 2 is arranged in a cross shape. This line resonator 2 is also formed by a dielectric waveguide, which is short-circuited at its ends 8. Pins 12 are also provided in the stray-field sensor 1 with a cross-shaped line resonator 2 for coupling the resonant electrical field of the line resonator 2 to the substance to be measured.

In the cross-shaped arrangement of the line resonator 2 in the stray-field sensor 1 according to FIG. 4, the pins 12 for coupling the stray field out into the outside space are disposed perpendicular to the line resonator 2, that is, perpendicular to the drawing plane of FIG. 4.

Figure 5:
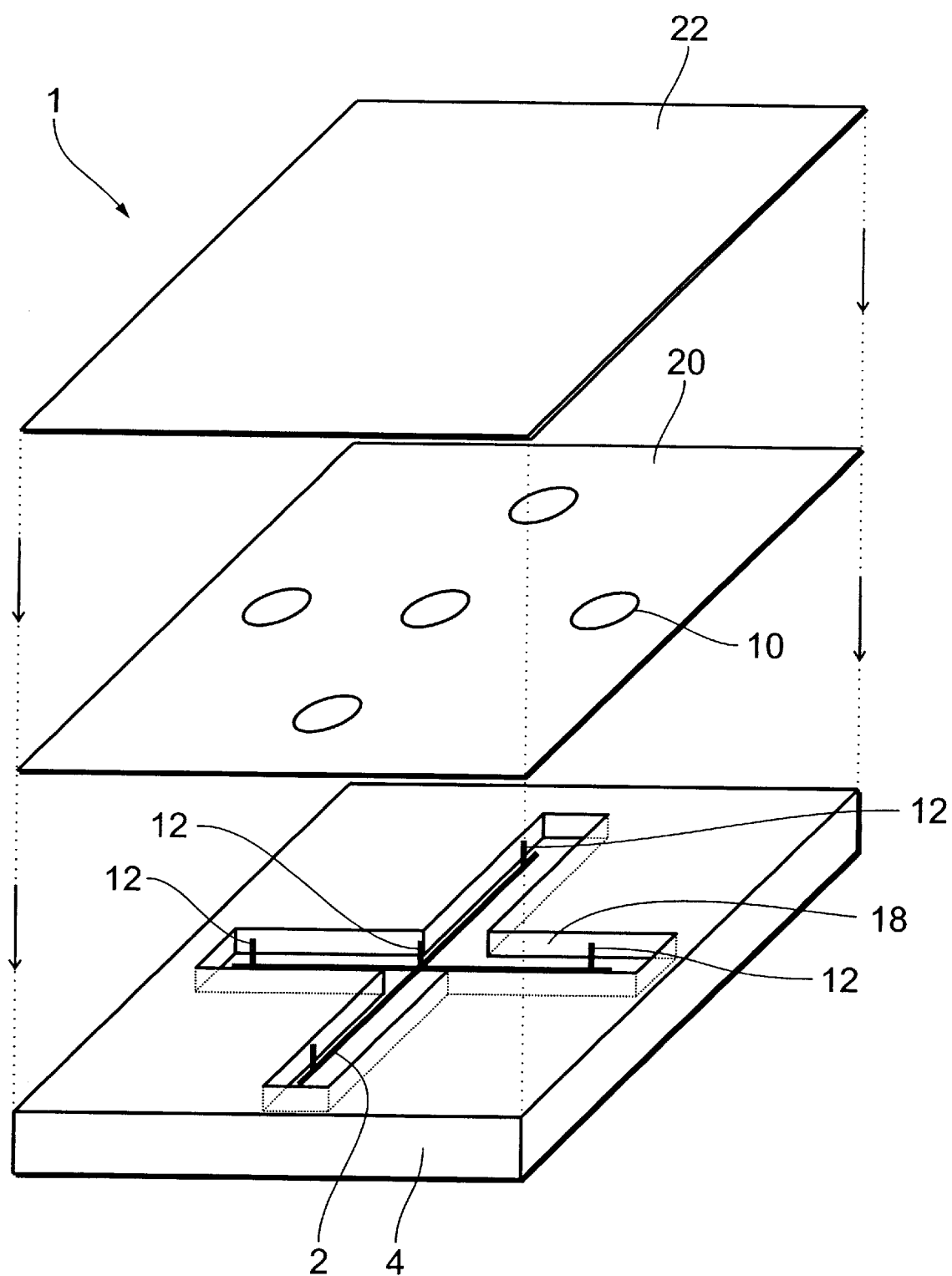
FIG. 5 is an exploded, perspective view of the embodiment according to FIG. 4.

FIG. 5 is a schematic, exploded view of the design of the stray-field sensor 1 from FIG. 4. Again, identical parts are provided with the same reference characters. FIG. 5 shows the housing 4. The line resonator 2 is embedded in a cross-shaped recess 18 in the housing 4. The perspective view of the line resonator 2 according to FIG. 5 clearly shows the pins 12, which are mounted at a right angle on the line resonator 2. The housing 4 of the stray-field sensor 1 illustrated in FIGS. 4 and 5 is flat, so it can be inserted into the aforementioned discharge walls for loose tobacco. A lid 20 is positioned on the housing 4. The lid 20 comprises an electrically-conductive material and has openings 10. The center point of the circular openings 10 lies exactly above the extended longitudinal axis of the pins 12. A closing plate 22 is located higher up in FIG. 5. This closing plate 22 comprises the aforementioned, non-conductive metallic PEEK material. The closing plate 22 serves to protect the recess 18 in the housing 4, the line resonator 2 with the pins 12, and the cover plate 20 from external influences.

Figure 6:
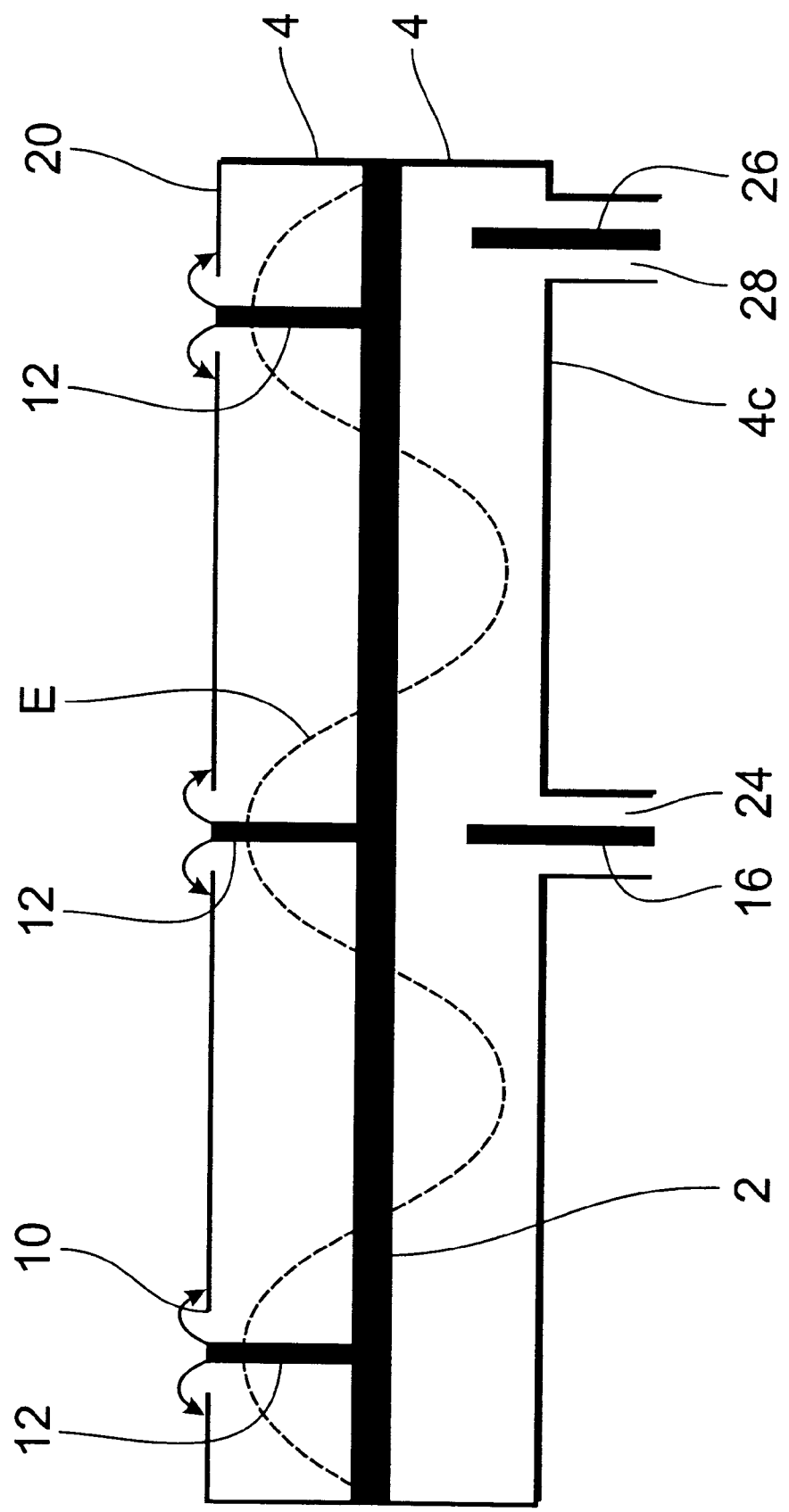
FIG. 6 is a side view of the embodiment according to FIG. 4 with an overlay of the electric field amplitude represented in dotted line.

FIG. 6 is a schematic side view of the stray-field sensor 1 shown in FIGS. 4 and 5. In this drawing, identical parts are provided with the same reference characters. The closing plate 22 is not shown in this representation. In addition to physical objects, FIG. 6 schematically indicates the electrical field E in dashed lines. FIG. 6 shows that the maxima of the electrical field E, which is made resonant by the line resonator 2, lie exactly at the positions of the pins 12 for coupling out the stray field represented by arched arrows. Because the maxima are of identical polarity (FIG. 1), only the stray field represented by the arrows is coupled to the outside through the openings 10 in the lid 20. No far field, i.e., a radiation loss, occurs for the aforementioned reasons.

For coupling in the field, a coupling-in antenna 16 is guided into the housing 4 through an opening 24. The coupling-in antenna 16 lies exactly beneath the pin 12 disposed in the center (FIG. 5). For coupling out, a coupling-out antenna 26 extends through an opening 28 cut into the edge of the lower wall 4c of the housing 4.

Figure 7:
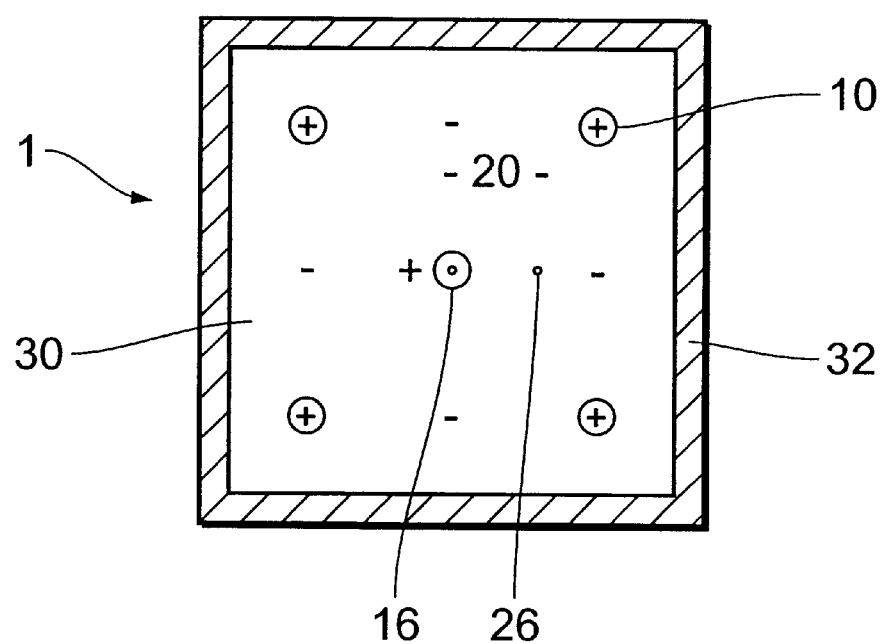
FIG. 7 is a schematic plan view of a further embodiment of the invention with a cavity resonator.

FIG. 7 schematically shows a stray-field sensor 1, which employs a cavity resonator 30. FIG. 7 depicts an H303 resonator. This means that three half-waves can propagate in the x and z direction, and no half-waves can propagate in the y direction (see the coordinate axes x, y, z in FIG. 7) in this resonator. Also in the cavity resonator 30 of FIG. 7, the coupling in or coupling out is effected via coupling antennas 16 and 26, respectively. In the relationship between the distance b' of the coupling-out antenna 26 from the side wall 32 of the cavity resonator 30 and the total width b of the cavity resonator 30 equals a ratio of 28/100.

The cavity resonator 30 according to FIG. 7 also has openings 10 in its lid 20. Beneath each opening is a Plexiglas cylinder, not shown, that respectively has an antenna, also not shown. The desired stray field can therefore be generated between the antenna and the lid 20. According to FIG. 7, only identical-polarity maxima of the electrical, resonant field are provided with an opening 10 to the outside.

Figure 8:
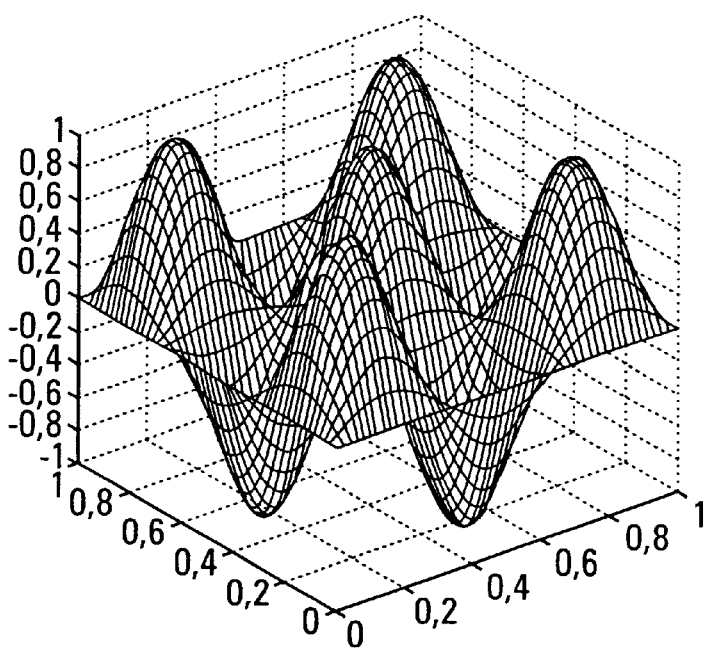
FIG. 8 is a three dimensional diagram showing the electrical field distribution of the cavity resonator according to FIG. 7.

FIG. 8 illustrates the electrical field distribution in a three-dimensional diagram, which includes the maxima of the electrical field indicated by the operational sign "+" in FIG. 7.

Other resonances besides the resonance H303 are present in the cavity resonator 30 shown in FIG. 8. All resonances with even numbers (e.g., H203, H204, H404, . . . ) can easily be suppressed, because they all have a zero value of the electrical field E in the center point, and the coupling is effected with the coupling-in antenna 16 at this location.

Figure 9:
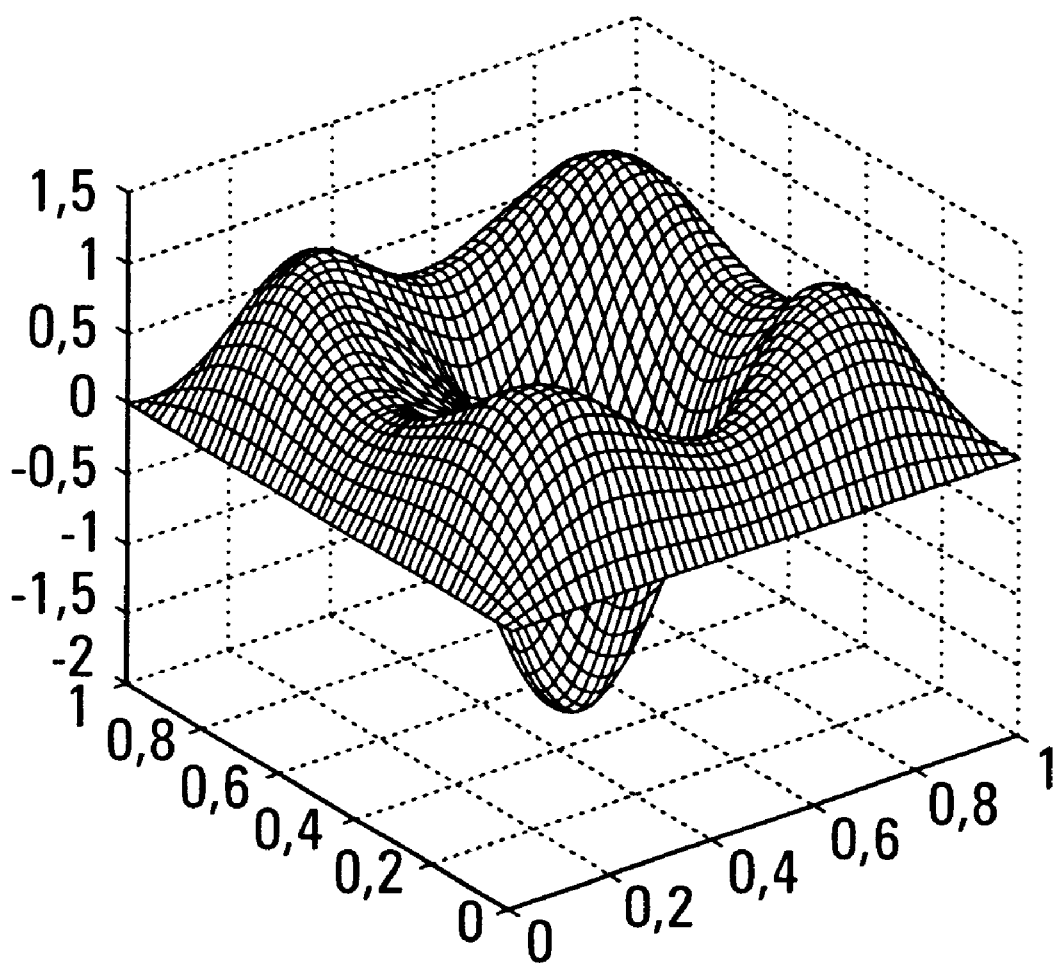
FIG. 9 is a three dimensional diagram showing an interfering field distribution of the cavity resonator according to FIG. 7.

An interfering resonance is superposed with H301 at H103, however. This resonance has a zero value of the electrical field E at about 28% of the total width on the axis of symmetry. For this reason, the coupling-out antenna 26 according to FIG. 7 is provided at 28% (b') of the total width b of the cavity resonator 30. This value can be determined experimentally for each cavity resonator 30. FIG. 9 illustrates the three-dimensional field distribution of the electrical field E at the resonance H103 with H301.

The invention has been described in detail with respect to referred embodiments, and it will now be apparent from the foregoing to those skilled in the art, that changes and modifications may be made without departing from the invention in its broader aspects, and the invention, therefore, as defined in the appended claims, is intended to cover all such changes and modifications that fall within the true spirit of the invention.

What is claimed is:

1. A stray-field sensor for measuring dielectric properties of substances, comprising:
   generating elements for generating an electrical field; and
   shielding elements for shielding the generated electrical field, the shielding elements having at least two openings at locations for coupling out the electric field such that a stray electric field extends at least partially outside of the shielding elements.

2. The stray-field sensor according to claim 1, wherein the openings are disposed in the shielding elements so that the electrical field is coupled out at locations of identical amplitude of the electric field.

3. The stray-field sensor according to claim 1, wherein the generating elements are configured so that the electrical field is in resonance.

4. The stray-field sensor according claim 1, wherein the generating elements are configured so that the electrical field is a high-frequency AC field.

5. The stray-field sensor according to claim 1, wherein the openings are located in the shield elements to that the electrical field is coupled out at amplitude maxima of the electric field.

6. The stray-field sensor according to claim 5, wherein the openings are located so that the electrical field is coupled out at the amplitude maxima of the electrical field having the same operational sign.

7. The stray-field sensor according to claim 1, wherein the shielding elements comprise a housing for the generating elements.

8. The stray-field sensor according to claim 1, wherein the openings each have a diameter that is small in comparison to a wavelength of the electrical field.

9. The stray-field sensor according to claim 1, wherein the generating elements comprise a waveguide.

10. The stray-field sensor according to claim 9, wherein the waveguide comprises a line resonator having two ends that are short-circuited ends.

11. The stray-field sensor according to claim 9, wherein the waveguide has a length of about $n \times \lambda/2$, with $n \leq 3$.

12. The stray-field sensor according to claim 11, wherein the waveguide has a length of about $n \times \lambda/2$, with $n \leq 10$.

13. The stray-field sensor according claim 9, wherein the waveguide has a meandering shape.

14. The stray-field sensor according to claim 11, wherein n is uneven, and the electrical field is coupled into a center of the waveguide.

15. The stray-field sensor according claim 9, wherein the waveguide has a cross shape.

16. The stray-field sensor according to claim 15, wherein each leg of the waveguide cross has a length corresponding to $5 \times \lambda/2$.

17. The stray-field sensor according to claim 9, wherein the waveguide is highly resistive.

18. The stray-field sensor according claim 9, wherein the waveguide has a longitudinal axis and includes pins mounted perpendicular to the longitudinal axis at the coupling-out locations of the electrical field.

19. The stray-field sensor according to claim 18, wherein the shielding elements comprise a housing having an outside wall and the pins bridge a distance between the waveguide within the housing and the outside housing wall.

20. The stray-field sensor according to claim 19, further comprising a measurement circuit having a measurement output for coupling out a measurement, the measurement output being positioned opposite the stray field coupling-out locations.

21. The stray-field sensor according to claim 20, wherein the measurement output is located at points that are arranged symmetrically relative to one another.

22. The stray-field sensor according to claim 1, wherein the generating elements comprise a cavity resonator.

23. The stray-field sensor according to claim 22, wherein the electrical field is coupled into the center of the cavity resonator.

24. The stray-field sensor according to claim 22, wherein the generating elements include antennas positioned at the coupling-out locations of the electrical field and inside the shielding elements, the antennas connecting the cavity resonator inside the shielding elements to an outside space for coupling the electrical field out into the outside space.

25. The stray-field sensor according to claim 24, wherein the antennas comprise cylinders including a dielectric material.

26. The stray-field sensor according to claim 24, wherein the cylinders are comprised of Plexiglas.

27. A method for measuring dielectric properties of substances, comprising:
   generating a resonant electrical field inside shielding elements;
   coupling out a portion of the resonant electrical field as a stray electric field through openings in the shielding elements at locations of identical-polarity maxima of the electrical field and into a space in which the substance to be examined is located; and
   measuring a change in the resonant frequency of the resonant electrical field.

* * * * *